United States Patent
Mixer, III et al.

(10) Patent No.: US 12,379,361 B2
(45) Date of Patent: Aug. 5, 2025

(54) REASSURANCE CONTROL SYSTEM AND METHOD

(71) Applicant: Powerex-Iwata Air Technology Inc., Harrison, OH (US)

(72) Inventors: Jon L. Mixer, III, Smyrna, TN (US); Jeffrey A. Heyser, Lebanon, OH (US); Joseph A. Abt, Harrison, OH (US)

(73) Assignee: Powerex-Iwata Air Technology Inc., Harrison, OH (US)

( * ) Notice: Subject to any disclaimer, the term of this patent is extended or adjusted under 35 U.S.C. 154(b) by 683 days.

(21) Appl. No.: 17/575,238

(22) Filed: Jan. 13, 2022

(65) Prior Publication Data
US 2022/0221436 A1    Jul. 14, 2022

Related U.S. Application Data

(60) Provisional application No. 63/137,319, filed on Jan. 14, 2021.

(51) Int. Cl.
*G01N 33/00* (2006.01)
(52) U.S. Cl.
CPC ..... *G01N 33/0062* (2013.01); *G01N 33/0063* (2013.01)
(58) Field of Classification Search
CPC ................ G01N 33/0062; G01N 33/0063
See application file for complete search history.

(56) References Cited

U.S. PATENT DOCUMENTS

| | | | | |
|---|---|---|---|---|
| 5,031,068 A | * | 7/1991 | Hansen, III | G01R 27/2605 324/684 |
| 10,240,723 B2 | * | 3/2019 | Huang | A61M 16/1005 |
| 10,983,513 B1 | * | 4/2021 | Al Kadem | G01F 5/005 |
| 2010/0312188 A1 | * | 12/2010 | Robertson | A61B 5/0006 600/300 |
| 2016/0209259 A1 | * | 7/2016 | Edwards | F17C 13/021 |

* cited by examiner

*Primary Examiner* — Manuel A Rivera Vargas
(74) *Attorney, Agent, or Firm* — Arnold & Porter Kaye Scholer LLP

(57) ABSTRACT

A reassurance control system and method of use thereof are disclosed herein. The reassurance control system comprising a controller, such as a programmable logic controller, having one or more import ports, wherein each of the one or more ports is assigned a fluid identity. The system further includes a transducer coupled to a fluid and to the controller via a first port having a first fluid identity of the one or more ports. The transducer produces and transmits an identity signal and a pressure signal to the controller. The controller matches the assigned fluid identity of the first port to the identity signal. Wherein responsive to the assigned fluid identity of the first port matching the identity signal, the controller based upon the received identity signal instructs a display to display an identity of the fluid and wherein based upon the received pressure signal displays a pressure of the fluid.

20 Claims, 10 Drawing Sheets

COMBO ALARM GAS SETUP

110

Press an entry or selection box directly below to enable override of default values.

| New | 1 | | ICU East Zone 2 | | RETURN LOW/HIGH & UOM TO DEFAULT | PSIG | SET TO ±20% CURRENT PRESSURE | 44.0 | 66.0 |
|---|---|---|---|---|---|---|---|---|---|

| No. | Edit | Gas Type | Location | UOM | LOW | HIGH |
|---|---|---|---|---|---|---|
| 1. | ✎ | OXYGEN | ICU East Zone 2 | PSIG | 44.0 | 66.0 |
| 2. | ✎ | MEDICAL AIR | ICU East Zone 2 | PSIG | 44.0 | 66.0 |
| 3. | ✎ | CARBON DIOXIDE | ICU East Zone 2 | PSIG | 40.0 | 60.0 |
| 4. | ✎ | NITROUS OXIDE | ICU East Zone 2 | PSIG | 40.0 | 60.0 |
| 5. | ✎ | NITROGEN | ICU East Zone 2 | PSIG | 140.0 | 200.0 |
| 6. | ✎ | MEDICAL VACUUM | ICU East Zone 2 | IN HG | 12.0 | 999.0 |

| HOME | SAVE | SETTINGS MENU | ALARM BADGE SETUP | MAINTENANCE MODE OFF |
|---|---|---|---|---|

FIG. 5

| MASTER ALARM | OXYGEN | MEDICAL AIR | CARBON DIOXIDE |
|---|---|---|---|
| OXYGEN | ICU East Zone 2 | ICU East Zone 2 | ICU East Zone 2 |
| MEDICAL AIR | 52 | 50 | 50 |
| NITROUS OXIDE | PSIG | PSIG | PSIG |
| MEDICAL VACUUM | MISMATCH | NORMAL | NORMAL |
| NITROGEN | NITROUS OXIDE | NITROGEN | MEDICAL VACUUM |
| CARBON DIOXIDE | ICU East Zone 2 | ICU East Zone 2 | ICU East Zone 2 |
| | 50 | 171 | 16 |
| | PSIG | PSIG | IN HG |
| | NORMAL | NORMAL | NORMAL |

Gas 1 Mismatch Alarm    Gas 1 Mismatch Alarm

FIG. 6

REASSURANCE CONTROL SYSTEM AND METHOD

CROSS REFERENCES TO RELATED APPLICATIONS

The following application claims priority under 35 U.S.C. 119(e) to U.S. Provisional Patent Application Ser. No. 63/137,319 filed Jan. 14, 2021 entitled REASSURANCE CONTROL SYSTEM AND METHOD. The above-identified application is incorporated herein by reference in its entirety for all purposes.

TECHNICAL FIELD

The present disclosure relates to a reassurance control system and method, and more particularly, a reassurance control system used to assure no mismatch of identified connection fluid and actual connection fluid.

BACKGROUND

When utilizing various fluids to be provided to a user or patient, specifically as used for medical gases in NFPA 99, it is advantageous and/or necessary to make sure that pressure transducers, custom designed circuit boards and/or programmable logic controller (PLC) circuits intended for use on one fluid are not accidentally applied to another. Typically, pressure transducers have a way of identifying themselves so that a PLC will recognize if a cross connection exists. In some instances pressure transducers, such as transducers using silicon wafer or other technologies, can be configured to utilize a low voltage input and generate an output that is proportional to an applied pressure or vacuum condition. The output can be a voltage or current value that is recognized by the analog input terminals of a custom designed circuit board and/or a PLC and displayed or used for any logic function.

Another typical output is a recognized output provided by a HART system, where a sine wave is superimposed on the output signal of the transducer, with the modulation of the sine wave frequency carrying identification information. To utilize the HART system the PLC analog input circuit must have a compatible HART recognition adapter as well.

Transducers typically lack identifying elements. One common method of manufacturing standard (non-identifying) transducers uses a 4 to 20 milliamp current that is proportional to the applied pressure, with 4 milliamps being generated when the pressure is at ambient condition, and 20 milliamps at whatever the maximum range is assigned to be.

SUMMARY

One aspect of the present disclosure includes a reassurance control system. The reassurance control system comprises a controller having one or more input ports, wherein each of the one or more ports is assigned a fluid identity. The reassurance control system further comprises a transducer coupled the controller via a first port of the one or more ports having a first fluid identity. The transducer produces an identity signal and a pressure signal and transmits the identity signal and pressure signal to the controller. The controller matches the assigned fluid identity of the first port to the identity signal. The reassurance control system additionally comprises a display coupled to and in communication with the controller, wherein responsive to a first fluid being coupled to the transducer and the assigned fluid identity of the first port matching the identity signal, the controller based upon the received identity signal displays an identity match of the fluid and wherein based upon the received pressure signal displays a pressure of the fluid.

Another aspect of the present disclosure includes a method of using a reassurance control system. The method comprises assigning fluid identity to a first import port of a controller having one or more import ports, a first fluid connector connected via a transducer to the first input port, the transducer coupled to the controller, and responsive to the assigned fluid identity of the first fluid, producing an identity signal and transmitting the identity signal to the controller. The method further comprises responsive to a pressure of the first fluid, producing a pressure signal and transmitting the pressure signal to the controller, responsive to matching the assigned first fluid identity of the first port to the identity signal, displaying an identity match of the fluid and wherein, based upon the received pressure signal, displaying a pressure of the fluid.

Yet another aspect of the present disclosure includes a reassurance control system. The system comprises a controller having one or more input ports, wherein each of the one or more input ports is assigned a fluid identity and a transducer coupled to the controller via a first port of the one or more ports. The first port has an assigned first fluid identity, the transducer produces a ready signal comprising a ready current for a ready duration, an identity signal comprises an identity current for an identity duration and a pressure signal compromising a pressure current proportional to the pressure of the first fluid for a pressure duration. The transducer transmitting the ready signal, the identity signal and the pressure signal to the controller, the controller matching the assigned first fluid identity of the first port to the identity signal. The system includes a display coupled to and in communication with the controller, wherein responsive to coupling a first fluid to the transducer and the assigned first fluid identity of the first port matching the identity signal, the controller, based upon the received identity signal, displays an identity match of the fluid and wherein, based upon the received pressure signal, displays a pressure of the fluid, responsive to the controller determining the assigned first fluid identity of the first port does not match the identity signal, the controller instructs the display to present an alarm.

BRIEF DESCRIPTION OF THE DRAWINGS

The foregoing and other features and advantages of the present disclosure will become apparent to one skilled in the art to which the present invention relates upon consideration of the following description of the invention with reference to the accompanying drawings, wherein like reference numerals refer to like parts unless described otherwise throughout the drawings and in which:

FIG. 5 is a front side elevation view of a display screen coupled to a gas distribution assembly, in accordance with one example embodiment;

FIG. 6 is a front side elevation view of a display screen coupled to a gas distribution assembly illustrating a mismatch, in accordance with one example embodiment;

Figure 1:
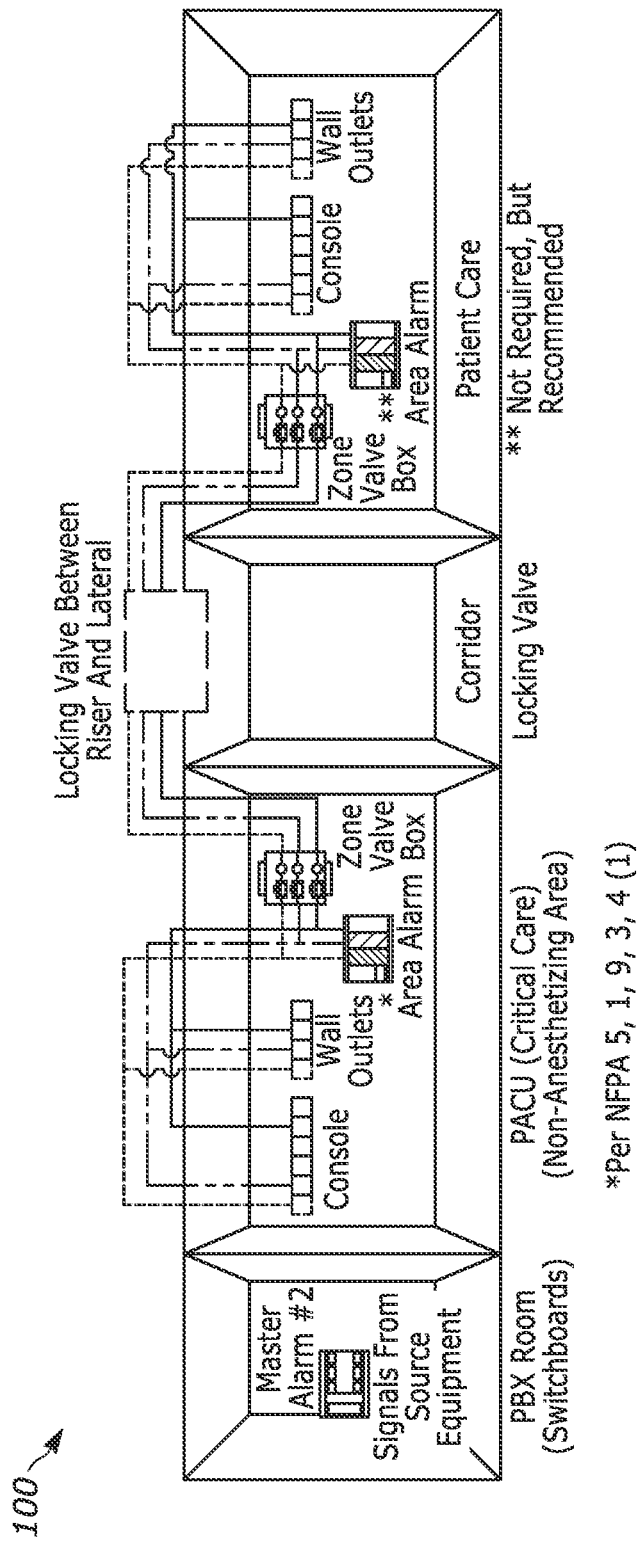
FIG. 1 is a schematic view of a portion of a gas distribution assembly having a display constructed in accordance with one example embodiment.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Referring now to the figures generally wherein like numbered features shown therein refer to like elements throughout unless otherwise noted. The present disclosure relates to a reassurance control system and method, and more particularly, a reassurance control system used to assure no mismatch of identified connection fluid and actual connection fluid.

Figure 2:
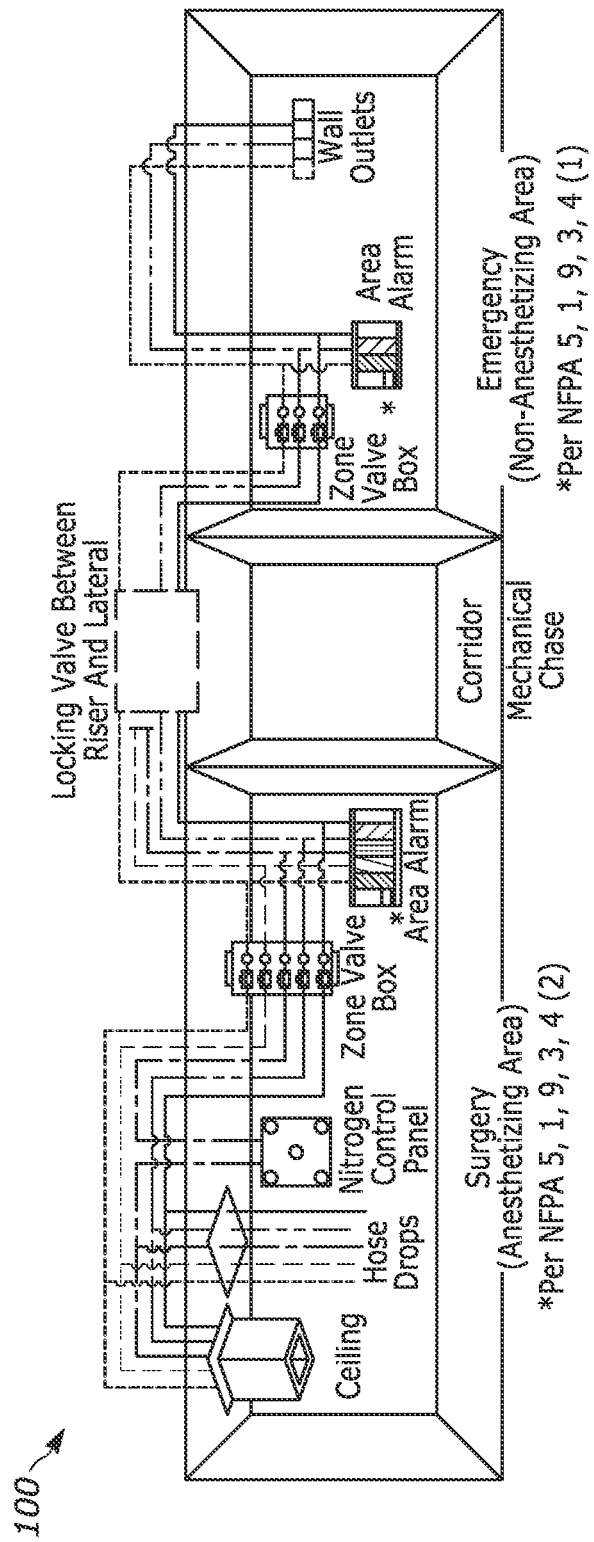
FIG. 2 is a schematic view of a portion of a gas distribution assembly having a display constructed in accordance with one example embodiment.
Figure 3:
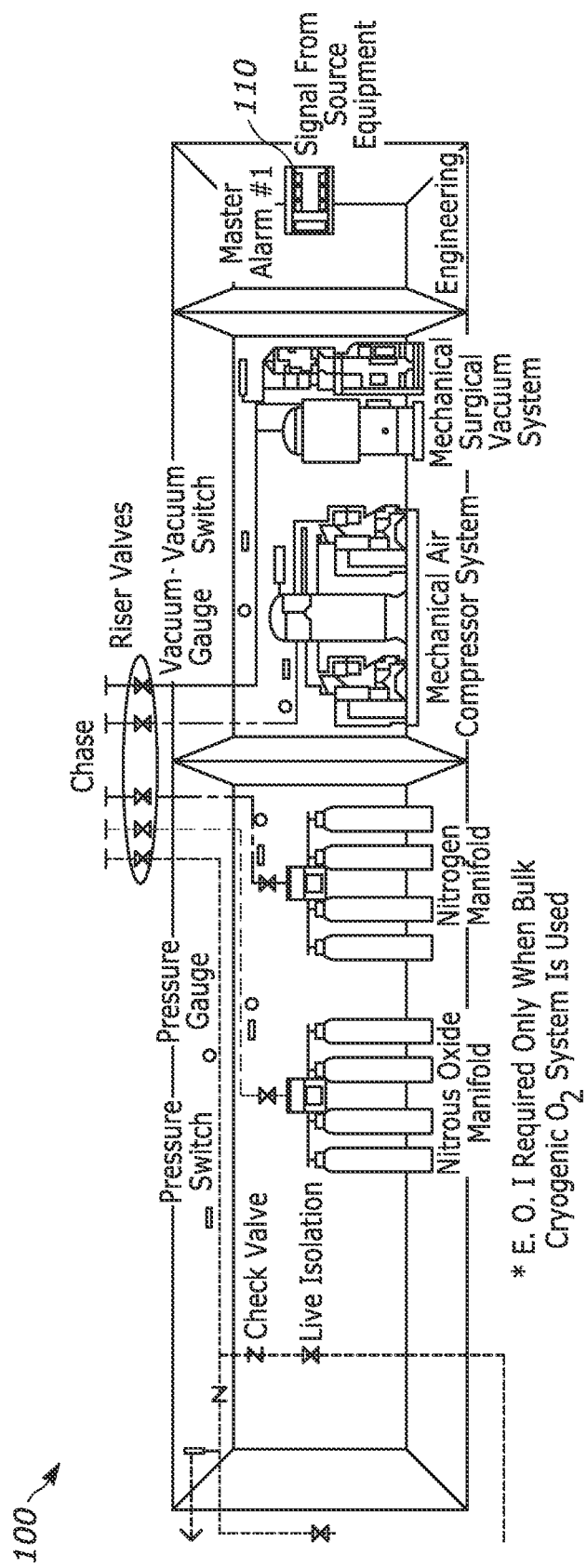
FIG. 3 is a schematic view of a portion of a gas distribution assembly having a display constructed in accordance with one example embodiment.

A reassurance control system 120 (see FIG. 7) involves utilizing a number of transducers 102, $102_2$, $102_n$, to transmit a pressure of an associated fluid (e.g., medical gasses, fluids, etc.), and to transmit an identity signal 210 (see FIG. 8), wherein a controller 108 is programed to verify the identity signal for each transducer of the number of transducers as identifying the associated fluid of each transducer. In the illustrated example embodiments of FIGS. 1-3, a gas distribution assembly 100 supporting the reassurance control system 120 is illustrated. It should be appreciated that the reassurance control system 120 can be used by any type of fluid or gas distribution system.

Figure 4:
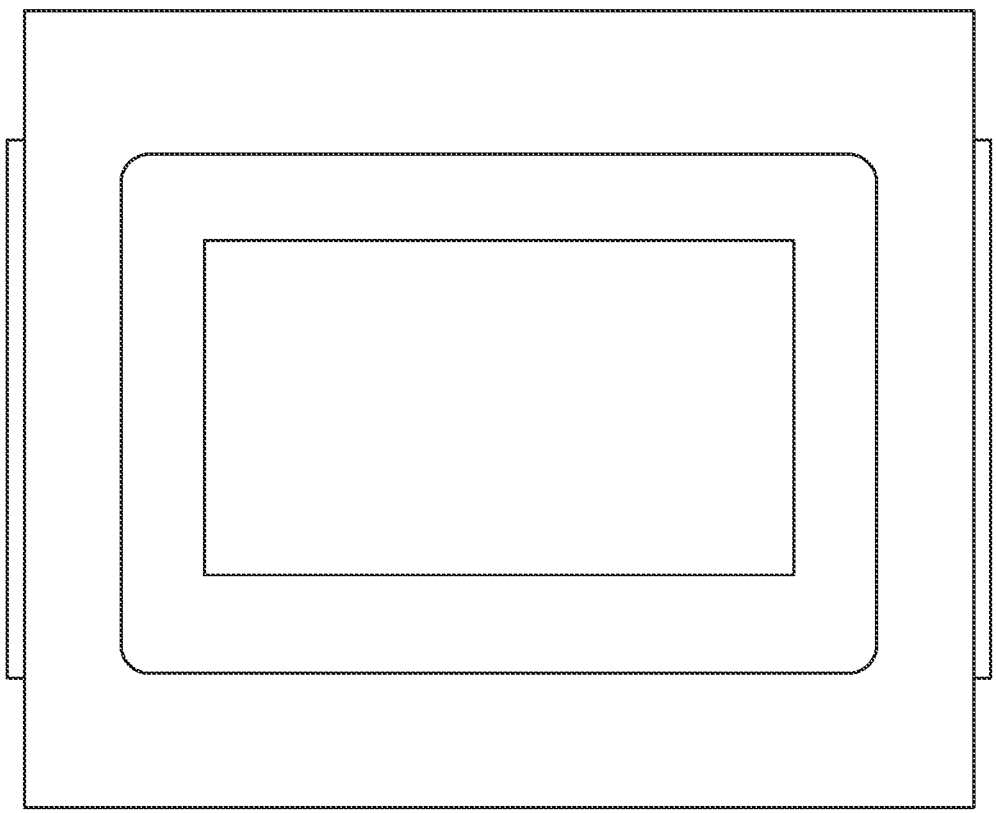
FIG. 4 is a front side elevation view of a display screen, in accordance with one example embodiment.
Figure 7:
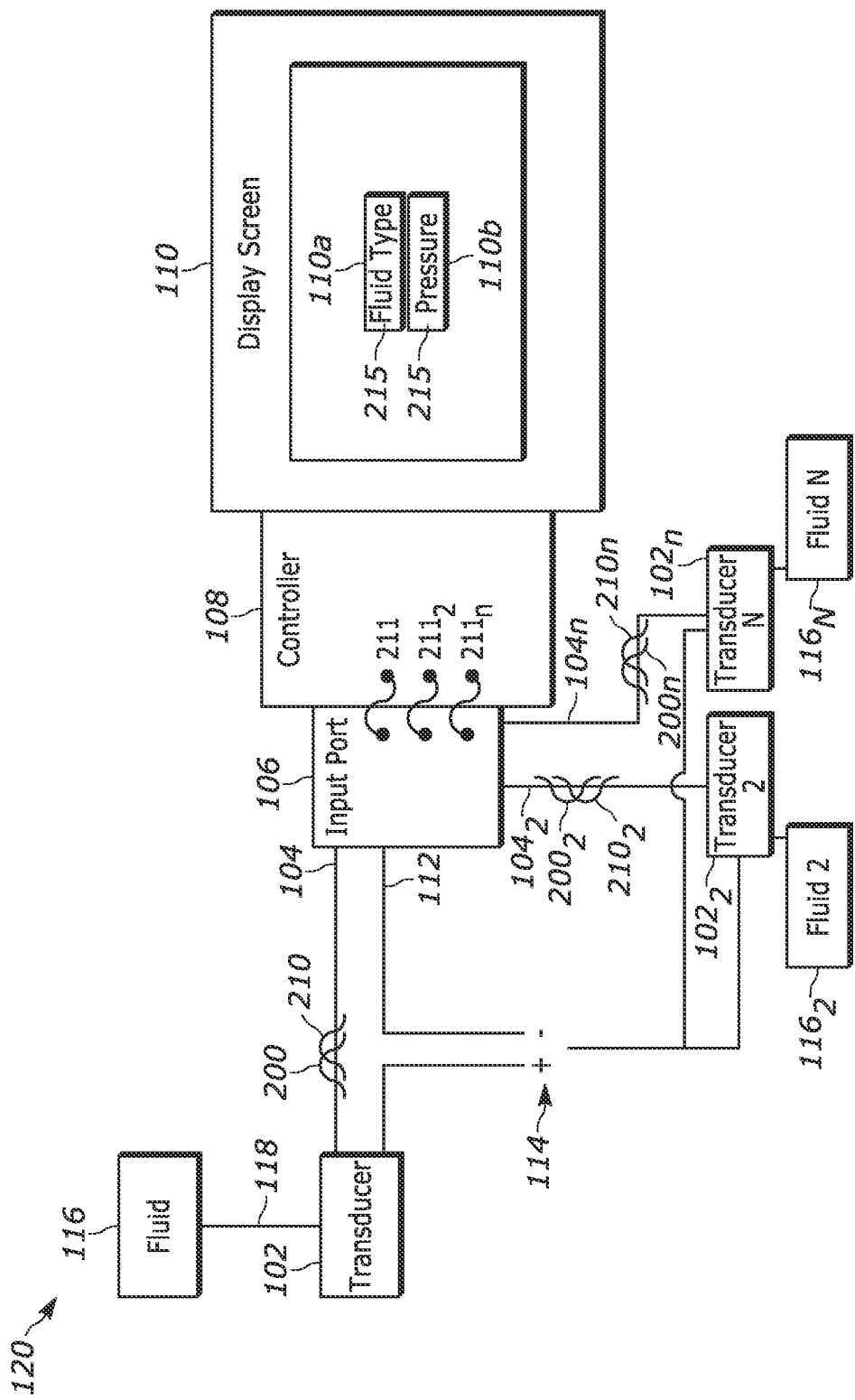
FIG. 7 is schematic diagram of a reassurance control system for use in a gas distribution assembly having a display, in accordance with one example embodiment.

Referring now to FIG. 7, the reassurance control system 120 is illustrated. In this example embodiment, the transducer 102 is coupled to a fluid 116 via a fluid connector 118. It should be appreciated that while one transducer 102 is being described, the system 120 is constructed to use and distinguish between an unlimited number of transducers 102, $102_2$, $102_n$ for different fluid types 116, $116_2$, $116_n$. The transducer 102 converts pressure (e.g., pressure of the fluid) into an electrical signal. Further, the transducer 102 is programed to include a signal 200, including the identity signal 210 (see FIG. 8, discussed in detail below). One example transducer is a transducer having part number ASI-471 made by Anfield Corporation. The transducer 102 is coupled to a power source 114 (e.g., a DC or AC voltage) and to an input channel 104 for coupling to an input port 106 of a controller 108. The input port 106 is also coupled to the power source 114. In one example embodiment, the controller 108 is a programmable logic controller (PLC) but could also be a personal or commercial computer or computing system. In this example embodiment, the controller 108 is programmed to recognize the identity signal 210. In one example embodiment, the controller 108 has multiple input ports 106, wherein each input port is programmed to recognize a different and/or unique identity signal 210 from different transducers 102, $102_2$, $102_n$. The controller 108 is coupled to and in communication with a display screen 110 (see, for example, FIG. 4). Wherein the display screen 110 coupled to the controller 108 displays an identified type of fluid 110a and/or the pressure 110b of the identified type of fluid 116 for each transducer 102, $102_2$, $102_n$ (see, for example, FIG. 5). Responsive to the identity signal 210 provided by the transducer 102 to the input port 104 not matching an identity signal check 211, $211_2$, $211_n$ programmed into the controller 108 received from the respective transducers 102, $102_2$, $102_n$ at the input port 106, the display screen 110 displays a mismatch alarm, and/or emits a mismatch alarm sound (see, for example, FIG. 6).

Figure 8:
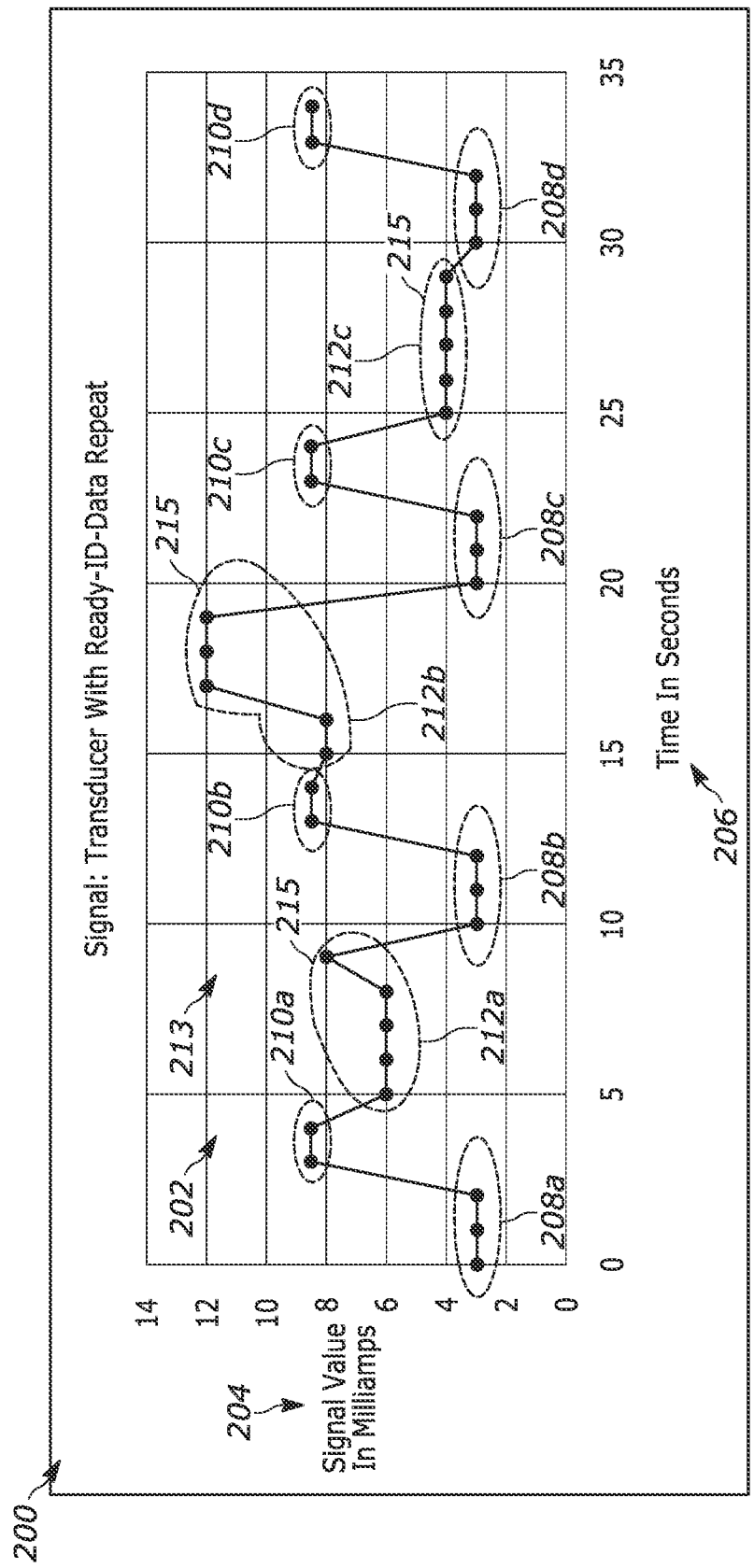
FIG. 8 is an example signal representation for use in a gas distribution assembly, in accordance with one example embodiment.

Illustrated in FIG. 8 is an example transducer 102 signal 200. The signal 200 includes data packets 213 of information 215, such as fluid types, fluid pressures, fluid temperature, fluid flow and/or the like. In FIG. 8, a y-axis 204 represents a signal value in milliamps and an x-axis 206 represents time in seconds. A signal line 202 represents the signal value in milliamps as time in seconds progresses. In this example embodiment, the signal line 202 represents a ready signal 208a at a first value (e.g., 3 milliamps) for a first duration (e.g., 3 seconds), followed by the identity signal 210a at a second value (e.g., 8.5 milliamps) for a second duration (e.g., 2 seconds). The signal line 202 proceeds with an information signal 215, such as a pressure signal 212a at a variable value for a third duration (e.g., 5 seconds). The signal line 202 continues, illustrating the ready signal 208b, 208c, 208d at the first value for the first duration, followed, respectively, by the identity signal 210b, 210c, 210d at the second value for the second duration. Each cycle of ready signal 208, and identity signal 210, is followed by a pressure value 212 (e.g., based on the variable pressure of the fluid 116) for the third duration. The signal line 202 cycle repeats until the fluid 116 is disconnected from the transducer 102 and/or the transducer is turned off. In another example embodiment, the signal line 202 cycle repeats until an identity duration is reached (e.g., 2 minutes) at which time the transducer 102 stops transmitting the ready signal 208 and the identity signal 210 and transmits solely the information signal 215, such as the pressure signal 212. A second fluid coupled to a second transducer $102_2$ would have a different signal line than the signal line 202. In one example embodiment, a second signal line 202 would have a second ready signal, a second identity signal, and a second pressure signal. In one example embodiment, the second signal line 202 would have the same ready signal 208, including the same first value and first duration. In another example embodiment, the second signal line 202 would have a different ready signal 208, including a different first value and/or first duration. In one example embodiment, the second identity signal would have a different second value and/or different second duration than the identity signal 210. A second information signal 215, such as pressure signal 212 remains a function of the information or pressure of the second fluid, while the duration of the second pressure signal 212 is at least one of the same or different than the third duration of the pressure signal 212. In one example embodiment, the values of the ready signal 208, the identity signal 210, and the information 215 or pressure signal 212 are between 0-20 milliamps. Additionally, in another example embodiment, the duration of the first duration (e.g., the duration of the ready signal 208) is between 0.5 seconds to about 5 seconds, the duration of the second duration (e.g., the duration of the identity signal 210) is between 1 seconds to about 6 seconds, and the duration of the third duration (e.g., the duration of the pressure signal 212) is between 2 seconds to about 10 seconds.

The controller 108 is programmed to receive a specific signal 200 for each input port 106, wherein the controller is pre-programmed with the first, second and third durations of the ready signal 208, the identity signal 210, and the pressure signal 212, further wherein the controller is pre-programmed with the values of the ready signal and the identity signal. The controller 108 is further programmed to display the information 215 signal and/or the pressure signal 212 as a pressure of the fluid 116 on the display screen 110 (see, for example, FIG. 5). As the controller 108 is programmable, and the transducer 102 is programmable, no additional parts are needed to confirm correct connection of the fluid 116 to the correct input port 106.

Stated another way, for the first duration of the ready signal 208 a portion of the display 110 devoted to identifying the type of fluid 116 would indicate "waiting" or "sensor not detected" or some other neutral condition. Once the second duration of the identity signal 210 commences (e.g., the controller 108 receives the identity signal), the controller 108 processes the identity signal (e.g., within milliseconds of the beginning of the second duration), and the display shows the type of fluid 116 (e.g., a gas type such as oxygen, nitrogen, air, or the like) associated with that transducer 102. In another embodiment, the display 110 shows identity match of the fluid 116, wherein the identity match indicates the matching fluid is coupled to the matching port 106. In one instance the identify match comprises continuing normal operation of the display 110. Additionally, in one example embodiment, the controller 108 is programmed to signal a mismatch, as illustrated in FIG. 6.

Responsive to the pressure value 212 of the signal 200 being sent to the controller 108 (e.g., after the first and second duration) a portion of the display 110 is updated to give the actual value of the pressure condition. After the conclusion of the first cycle of the first, second and third durations, the current pressure value is not available, as the second cycle of the ready signal 208b, and the identity signal 210b are being transmitted for the first and second durations, the display 110 displays the last known pressure value. While the pressure was used in the current example, it would be appreciated that other information 215 could be presented individually or in combination with pressure. Such information 215 includes temperature, volumetric flow rate and/or the like.

Figure 9:
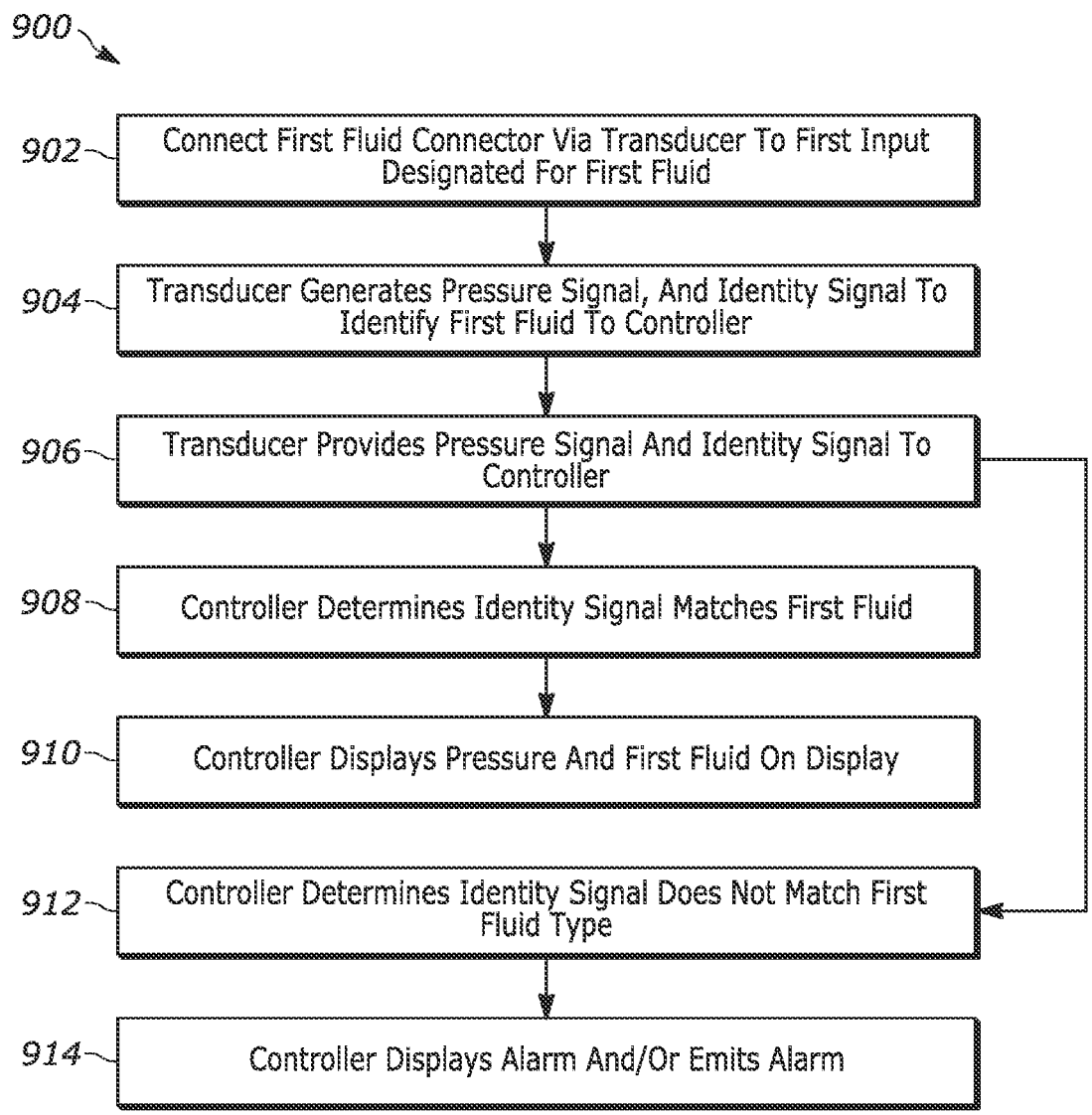
FIG. 9 is a flow chart illustrating a process of connecting and identifying inputs in a gas distribution assembly, in accordance with one example embodiment of the present disclosure.

Turning to FIG. 9 a method 900 of connecting the fluid 116, coupled to the transducer 102, to the controller 108 is illustrated. At 902, a fluid connector 118 is connected via the transducer 102 to a first input 106 designated for a first fluid. For example, the fluid connector 118 is connected to oxygen, and the first input 106 is designated for oxygen. At 904, the transducer 102 generates the signal 200 and the identity signal 210 and the pressure signal 212 in a repeating cycle to identify the first fluid to the controller 102. In another example embodiment, the repeating cycle of the transducer 102 includes the ready signal 208, prior to the identity signal 210. At 906, the transducer 102 provides the identity signal 210 and the pressure signal 212 to the controller 108. In this example embodiment, the identify signal 210 and the pressure signal 212 are provided to the controller in a repeating cycle (see FIG. 8). In another example embodiment, the repeating cycle provided to the controller 108 includes the ready signal 208, prior to the identity signal 210.

At 908, the controller 108 determines that the identity signal 210 matches the first fluid (e.g., the first fluid is oxygen and the identity signal is for oxygen). At 910, the controller 108 displays on the display 110 the pressure (determined from the pressure signal 212) and the first fluid (determined from the identity signal). At 912, the controller 108 determines that the identity signal 210 does not match the first fluid (e.g., the first fluid is nitrogen and the identity signal is for oxygen). At 914, the controller 108 displays on the display 110 an alarm indicating the mismatch and/or emits an alarm indicating the mismatch (see, for example, FIG. 6).

Figure 10:
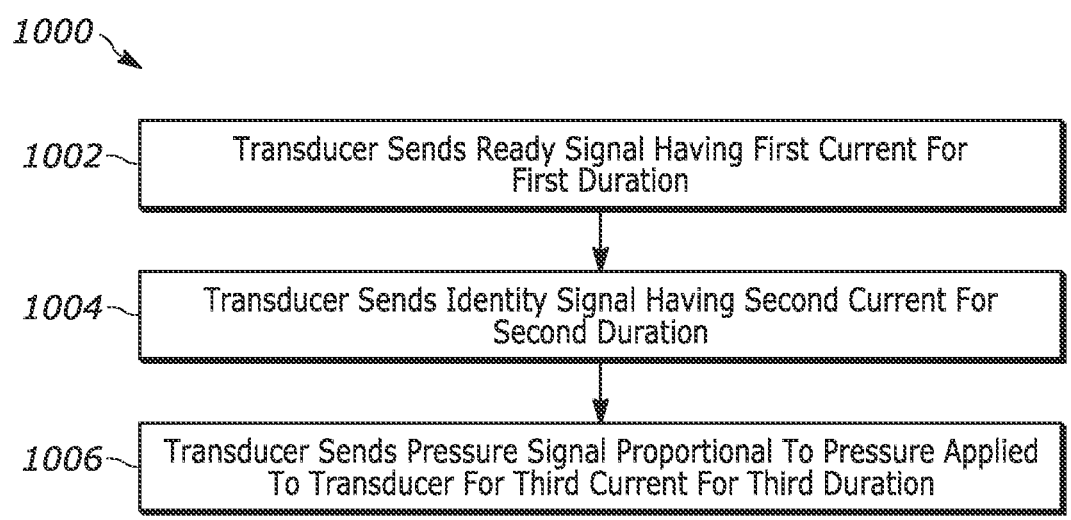
FIG. 10 is a flow chart illustrating a process of a controller receiving information from an input in a gas distribution assembly, in accordance with one example embodiment of the present disclosure.

Turning to FIG. 10, a method 1000 of using the transducer 102 to send one or more signals is illustrated. At 1002, the transducer 102 sends the ready signal 208 having a first current (e.g., value) for the first duration to the controller 108. At 1004, the transducer 102 sends the identity signal 210 having a second current (e.g., value) for the second duration to the controller 108. In one example embodiment, the first duration and the second duration are different, and/or the first current and the second current are different. At 1006, the transducer 102 sends the pressure signal 212 having a third current, which is proportional to the pressure being applied to the transducer, for the third duration to the controller 108. In one example embodiment, steps 1002-1006 repeat until the transducer 102 is decoupled from the fluid 116 and/or powered off. In one example embodiment, the first, second, and third durations are different.

The reassurance control system 120 utilizing the programmed transducer 102 allows for the production of alarm panels that meet NFPA 99 requirements without requiring the use of custom circuit boards. Further, any controller 108 (such as a PLC) with analog input ports 106 is configurable to function using the signal 200. The reassurance control system 120 provides an advantage in product design flexibility, reduced development time, and compatibility with applicable safety standards, as the controllers 108 will typically be already in compliance with the applicable safety standards. Further, using existing controllers 108 removes the need to show compliance with custom circuit boards, which is difficult and expensive.

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. In one non-limiting embodiment the terms are defined to be within for example 10%, in another possible embodiment within 5%, in another possible embodiment within 1%, and in another possible embodiment within 0.5%. The term "coupled" as used herein is defined as connected or in contact either temporarily or permanently, although not necessarily directly and not necessarily mechanically. A device or structure that is "configured" in a certain way is configured in at least that way, but may also be configured in ways that are not listed.

To the extent that the materials for any of the foregoing embodiments or components thereof are not specified, it is to be appreciated that suitable materials would be known by one of ordinary skill in the art for the intended purposes.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A reassurance control system, the system comprising:
a controller having one or more input ports, wherein each of the one or more input ports is assigned a fluid identity;
a transducer coupled to the controller via a first port of the one or more ports, the first port having an assigned first fluid identity, the transducer producing an identity signal and a pressure signal and transmitting the identity signal and pressure signal to the controller, the controller matching the assigned first fluid identity of the first port to the identity signal;
a second transducer coupled to the controller via a second port of the one or more ports, the second port having an assigned second fluid identity, the second transducer producing a second identity signal and a second pressure signal and transmitting the second identity signal and pressure signal to the controller, the controller matching the assigned second fluid identity of the second port to the second identity signal; and
a display coupled to and in communication with the controller, wherein responsive to coupling a first fluid to the transducer and the assigned first fluid identity of the first port matching the identity signal, the controller, based upon the received identity signal, displays an identity match of the fluid and wherein, based upon the received pressure signal, displays a pressure of the fluid.

2. The reassurance control system of claim 1, wherein said identity signal comprises the transducer transmitting an identity current for an identity duration.

3. The reassurance control system of claim 2, wherein said pressure signal comprises the transducer transmitting a pressure current that is proportional to the pressure of the fluid for a pressure duration.

4. The reassurance control system of claim 3, wherein the transducer transmits a ready signal, the ready signal comprising a transmission of a ready current for a ready duration, the ready signal proceeding the identity signal, and the identity current different than the ready current.

5. The reassurance control system of claim 1, wherein responsive to coupling the second fluid to the second transducer and the assigned second fluid identity of the second port matching the second identity signal, the controller, based upon a received second identity signal, displays an identity match of the second fluid and wherein, based upon a received pressure signal, displays a pressure of the second fluid.

6. The reassurance control system of claim 5, wherein said identity signal comprises the transducer transmitting an identity current for an identity duration, and the second identity signal comprises the second transducer transmitting a second identity current for a second identity duration, the identity current different from the a second identity current.

7. The reassurance control system of claim 6, wherein the transducer and the second transducer transmit a ready signal, the ready signal comprising a transmission of a ready current for a ready duration, the ready signal proceeding the identity signal and the second identity signal, respectively, and the identity current and the second identity current different than the ready current.

8. The reassurance control system of claim 1, wherein responsive to the controller determining the assigned first fluid identity of the first port does not match the identity signal, the controller instructs the display to present an alarm.

9. The reassurance control system of claim 1, wherein the controller is a programmable logic controller.

10. A method of using a reassurance control system, the method comprising:
assigning a unique fluid identity to each of one or more import ports of a controller, wherein assigning a unique fluid identity to each of the one or more import ports of the controller includes assigning a first fluid identity to a first import port of the controller, wherein the controller further comprises a first fluid connected via a transducer to the first input port, the transducer coupled to the controller;
producing an identity signal based on the assigned first fluid identity and transmitting the identity signal to the controller;
producing a pressure signal based on a pressure of a fluid and transmitting the pressure signal to the controller; and responsive to the controller matching the assigned first fluid identity of the first port to the identity signal, displaying an identity match of the fluid and, based upon the received pressure signal, displaying a pressure of the fluid.

11. The method of claim 10, comprising producing a ready signal and transmitting the ready signal to the controller.

12. The method of claim 11, comprising transmitting the ready signal immediately prior to the identity signal, and transmitting the identity signal immediately prior to the pressure signal.

13. The method of claim 10, wherein responsive to the controller determining the assigned first fluid identity of the first port does not match the identity signal, instructing the display to present an alarm.

14. The method of claim 10, the producing the identity signal comprising producing an identity current for an identity duration and the producing a pressure signal comprising producing a pressure current proportional to the pressure of the first fluid for a pressure duration, the pressure duration different than the identity duration.

15. The method of claim 10, comprising producing a ready signal by producing a ready current for a ready duration, the ready duration different than the identity duration.

16. The method of claim 10, comprising producing a ready signal by producing a ready current for a ready duration, the ready current different than the identity current.

17. The method of claim 10, further comprising determining if the unique fluid identities match unique identity signals of one or more fluid connectors coupled to the one or more ports to generate an identity match.

18. A reassurance control system, the system comprising:
a controller having one or more input ports, wherein each of the one or more input ports is assigned a fluid identity;
a transducer coupled to the controller via a first port of the one or more ports, the first port having an assigned first fluid identity corresponding to a first fluid, the transducer producing a ready signal comprising a ready current for a ready duration, an identity signal comprising an identity current for an identity duration and a pressure signal comprising a pressure current proportional to the pressure of the first fluid for a pressure duration, and transmitting the ready signal, the identity signal, and the pressure signal to the controller, the controller matching the assigned first fluid identity of the first port to the identity signal; and
a display coupled to and in communication with the controller, wherein responsive to coupling a first fluid to the transducer and the assigned first fluid identity of the first port matching the identity signal, the controller, based upon the received identity signal, displays an identity match of the fluid and wherein, based upon the received pressure signal, displays a pressure of the fluid, responsive to the controller determining the assigned first fluid identity of the first port does not match the identity signal, the controller instructs the display to present an alarm.

19. The reassurance control system of claim 18, wherein the transmission of the ready signal precedes transmission of the identity signal, and wherein the identity current is different than the ready current.

20. The reassurance control system of claim 18, wherein the controller is a programmable logic controller.

* * * * *